United States Patent [19]

Nardella

[11] Patent Number: 5,357,956
[45] Date of Patent: Oct. 25, 1994

[54] APPARATUS AND METHOD FOR MONITORING ENDOCARDIAL SIGNAL DURING ABLATION

[75] Inventor: Paul C. Nardella, North Easton, Mass.

[73] Assignee: American Cardiac Ablation Co., Inc., Taunton, Mass.

[21] Appl. No.: 975,382

[22] Filed: Nov. 13, 1992

[51] Int. Cl.$^5$ .............................................. A61B 5/04
[52] U.S. Cl. .................................. 128/642; 128/702; 607/9
[58] Field of Search ...................... 128/642, 696, 702; 607/119, 122, 123, 125, 126, 128, 130, 28, 9

[56] References Cited

U.S. PATENT DOCUMENTS

| | | |
|---|---|---|
| 3,960,141 | 6/1976 | Bolduc . |
| 4,416,276 | 11/1983 | Newton et al. ................. 128/303.13 |
| 4,641,649 | 2/1987 | Walinsky et al. ................. 128/303.1 |
| 4,660,571 | 4/1987 | Hess et al. ........................ 128/642 X |
| 4,785,815 | 11/1988 | Cohen ................................. 128/642 |
| 4,805,621 | 2/1989 | Heinze et al. . |
| 4,869,248 | 9/1989 | Narula ............................ 128/303.13 |
| 4,896,671 | 1/1990 | Cunningham et al. ............. 128/642 |
| 4,945,912 | 8/1990 | Langberg .............................. 128/642 |
| 4,966,597 | 10/1990 | Cosman ................................ 606/50 |
| 5,156,151 | 10/1992 | Imran .................................... 128/642 |
| 5,239,999 | 8/1993 | Imran .................................... 128/642 |

OTHER PUBLICATIONS

Nardella, Paul C., "Radio Frequency Energy and Impedance Feedback", SPIE vol. 1068 Catheter-Based Sensing and Imaging Technology (1989).

Primary Examiner—Lee S. Cohen
Assistant Examiner—Jeffrey R. Jastrzab
Attorney, Agent, or Firm—Lahive & Cockfield

[57] ABSTRACT

An ablation catheter has an ablation electrode at a distal end coupled to an ablation power source through a low impedance coupling. The ablation electrode also functions as a sensing electrode, for monitoring the endocardial signal and preferably also tissue impedance during the ablation procedure, and is coupled to an electrode monitor through a high impedance coupling. A timing element operates a plurality of switches to selectively isolate, dampen, or interconnect various signal paths during plural repetitive non-overlapping ablation and quiescent intervals which alternate at a rate substantially above a Nyquist sampling rate. RF energy is delivered to the ablation site during the ablation intervals. The local endocardial signal is measured during the quiescent intervals.

22 Claims, 4 Drawing Sheets

APPARATUS AND METHOD FOR MONITORING ENDOCARDIAL SIGNAL DURING ABLATION

BACKGROUND OF THE INVENTION

The invention relates to an electrosurgical device, in the form of a catheter, and instrumentation for use in performing tissue ablation.

The ablation of organ tissue can be performed during surgical procedures to treat disease or medical disorders. Ablation of certain cardiac tissue is performed with increasing frequency to treat certain heart disorders which result in arrhythmia.

The heart is a muscular organ comprising four separate chambers which cooperate to pump blood throughout the body. The heart muscles must contract and relax in a coordinated sequence in order for blood to be passed through the circulatory system in an efficient manner. The heart includes a specialized system for generating impulses to cause rhythmical contraction of the heart muscle and for conducting these impulses rapidly through the heart. In the proper sequence the atria contract about one sixth of a second prior to the ventricles. This enables extra filling of the ventricles before they contract to pump blood through the lungs and to other areas of the body.

The basic timing impulse of the heart is generated in the sinoatrial node (SA node). The SA node has an inherent rhythm which can be modified by the sympathetic and parasympathetic nervous system. The impulse initiated by the SA node spreads through the atrium to the atrio-ventricular node (AV node), and then through the Purkinje fibers to the endocardial surfaces of the ventricles.

The rhythmical and conduction system of the heart is susceptible to disruption by disease. Damage caused to cardiac tissue can result in the inability of the cardiac conduction pathways to properly transmit the electrical impulses generated in the SA node, leading to arrhythmias, or irregular heartbeats. Cardiac arrhythmias can often be detected through electrocardiograms.

Some forms of cardiac arrhythmia are able to be controlled through medication. However, other forms of arrhythmia do not respond to medication. Moreover, medication typically does not cure the problem, and the dosage and the medication type must be changed periodically to maintain a continued level of control of the problem.

One alternative to medication is the surgical removal of a portion of the cardiac pathway which is responsible for the arrhythmia. The many dangers associated with open heart surgery render this a less preferred treatment option. Recently, however, it has become possible to intravascularly insert a specialized catheter within the heart, for positioning adjacent to the conductive tissue responsible for the arrhythmia. The catheter is adapted to deliver energy (e.g., radio frequency energy) to ablate or destroy the tissue lesion responsible for an arrhythmia. This has been found to be a relatively safe and effective technique for eliminating many causes of arrhythmia. Various ablation catheters and techniques for their use are described in U.S. Pat. Nos. 4,641,649; 4,785,815; 4,869,248; and 4,896,671.

Cardiac ablation catheters typically have at least one ablation electrode, positioned at the distal end of the catheter, which is adapted to deliver energy to the tissue lesion. Other electrodes can be proximally positioned on the catheter and used for sensing endocardial signals. Ablation may be achieved by the application of electrical energy, such as radio frequency (RF) or direct current (DC) energy, from a generator source, through a conductor disposed within the catheter, and to the ablation electrode.

During the ablation procedure, the ablation electrode is positioned adjacent to an ablation site, or site of defective tissue. The processes for accurately positioning the ablation electrode and "mapping" the ablation site are well known, and generally involve positioning a multi-electrode "mapping catheter," which may include an ablation tip, near the lesion, and radiographically visualizing the catheter position while simultaneously electrically monitoring the heart tissue. Once the ablation electrode is accurately positioned, energy, typically in the form of RF energy, is delivered to the ablation site by the ablation electrode.

The goal of the ablation procedure is to precisely destroy the defective tissue without damaging any healthy heart tissue. To prevent inadvertent damage of healthy tissue, it is desirable to monitor both the endocardial signal and the impedance at the ablation site during the ablation procedure. Monitoring is normally performed by one or more sensing electrodes proximally positioned on the catheter some distance away from the ablation electrode. Thus, in prior ablation systems, monitoring is not performed directly at the ablation site. This spatial discrepancy can result in an imprecisely controlled ablation procedure which may damage some healthy tissue, or fail to remove some of the defective tissue.

It would thus be advantageous to develop an ablation catheter system, suitable for use in cardiac ablation procedures, which measures the local impedance and the local endocardial signal directly at the ablation site. It would also be advantageous to develop a system that performs these measurements simultaneously with ablation.

SUMMARY OF THE INVENTION

It is thus an object of the invention to provide a catheter suitable for use with cardiac ablation procedures utilizing the delivery of RF energy. A further object is to provide an ablation catheter which provides accurate local monitoring of impedance and the endocardial signal at the ablation site, and during an ablation operation. It is also an object of the invention to provide a method for using such a catheter. Other objects will be apparent upon reading the disclosure which follows.

The present invention comprises an ablation catheter having an ablation electrode mounted at a distal end of the catheter and designed to allow positioning of the ablation electrode adjacent to cardiac tissue. The ablation electrode is coupled to a remote ablation power source through a low impedance coupling. The ablation electrode also functions as a sensing electrode, for monitoring the endocardial signal and preferably also the impedance during the ablation procedure, and is coupled to an electrode monitor through a high impedance coupling. A timing element defines plural repetitive ablation intervals which alternate in non-overlapping fashion with a similar plurality of quiescent intervals. RF energy is delivered to the ablation site during the ablation intervals, while the local endocardial signal is measured during the quiescent intervals.

In one embodiment a first switch element is connected between the low impedance coupling and the ablation electrode and is controlled by the timing element to connect the ablation electrode to the power source during ablation intervals, and to disconnect the electrode from the coupling during quiescent intervals. A second switch element is connected between the electrode monitor and the high impedance coupling and is controlled by the timing element to isolate the monitor from the electrode during ablation intervals and to couple them during quiescent intervals.

In another embodiment of the invention a low-pass filter and an amplifier are connected between the second switch element and the electrode monitor for improving the quality of the measured endocardial signal. In this embodiment, a third switch element, connected between the amplifier and the electrode monitor, is switched synchronously with the second switch element.

In one preferred embodiment, the RF power source provides a fifty volt square wave ablation power signal at RF frequency. The low impedance coupling efficiently transmits this RF power to the ablation electrode. The high impedance coupling is of a type that presents a high impedance at the RF frequency of the power source, and also allows detection of the low voltage endocardial signal so it can be measured accurately.

In the practice of a preferred ablation method, electrodes mounted exterior to the chest are actuated to artificially pace the heart so that it beats about 120 times per minute during the ablation procedure. The ablation electrode is positioned adjacent to the ablation site, and delivery of RF energy to the tissue lesion is initiated. The catheter may have a deflectable catheter tip, with its tip electrode spring-loaded outwardly to assure good electrode contact even when the heart moves during the ablation intervals.

The invention also contemplates another method when ablation only occurs while the heart is in a desired part of the cardiac cycle. According to this aspect of the invention, the ablation power intervals are triggered by timing pulses synchronized with detection of the R wave. This mode of actuation assures that the heart is essentially stationary before delivery of ablation energy, thus minimizing the risk of inadvertently ablating healthy tissue.

In yet a further aspect of a preferred method, the impedance at the ablation site is measured during the ablation intervals. As is well known, the tissue impedance can vary according to several factors such as the fatty tissue distribution in the patient, or the location of the electrode. However, once ablation commences, changes in impedance reflect the heating of tissue, denaturing of cellular material, and loss of water from heated tissue, thus reflecting the degree of ablation of surrounding tissue. Information on changes in tissue impedance, taken together with continuous monitoring of an arrhythmic signal, therefore indicates whether the tissue has been correctly targeted and sufficiently treated. Thus the impedance along with the measured endocardial signal provide information for determining when the ablation procedure is complete.

In the preferred method and system of the invention, ablation energy is delivered to the ablation site, during a plurality of short, closely-spaced, ablation intervals, until the monitored endocardial signal is free of indications of the arrhythmia. The ablation procedure is normally performed in less than approximately six seconds, and after such treatment, the absence of the arrhythmia signal usually means that the defective tissue has been destroyed. However, improper positioning of the ablation electrode may result in delivery of an insufficient level of power to the tissue, only stunning, rather than destroying, the defective tissue. Such stunning may cause the arrhythmia signal to temporarily disappear, so to assure that a lesion has been created in the defective tissue, it is preferred to wait about thirty minutes after the disappearance of the arrhythmia signal before withdrawal of the catheter. If the arrhythmia signal does not return within thirty minutes, there is a high confidence level that the lesion has been created, and the catheter is then withdrawn. If the arrhythmia signal does return, the ablation electrode is readjusted and the ablation procedure is repeated.

The endocardial signal is primarily a low frequency signal having most of its components below several hundred Hz. The highest frequency components of the signal are in the His-bundle and are about five hundred Hz. These latter signals are the principal ones detectable in arrhythmia sites. For accurate observation of the endocardial signal, applicant samples it at least one thousand times per second, to achieve Nyquist sampling of at least twice the frequency of the highest frequency component.

In one preferred method, the ablation and quiescent intervals alternate five thousand times per second, and the endocardial signal is sampled once during each quiescent interval. The quiescent intervals last for about fifty microseconds, and the ablation intervals last for about one hundred fifty microseconds. By switching the ablation electrode on and off at the preferred sampling frequency of five thousand times a second, and sampling the endocardial signal and tissue impedance between active intervals, significantly faster than the Nyquist rate, applicant avoids inducing muscle stimulation in the heart. Applicant avoids switching at a lower frequency of about 500 Hz, which would induce muscle contraction in the heart tissue.

BRIEF DESCRIPTION OF THE DRAWINGS

The foregoing features of the invention will be understood from the detailed description of illustrative embodiments to follow, together with the drawings wherein.

DETAILED DESCRIPTION OF THE INVENTION

Figure 1:
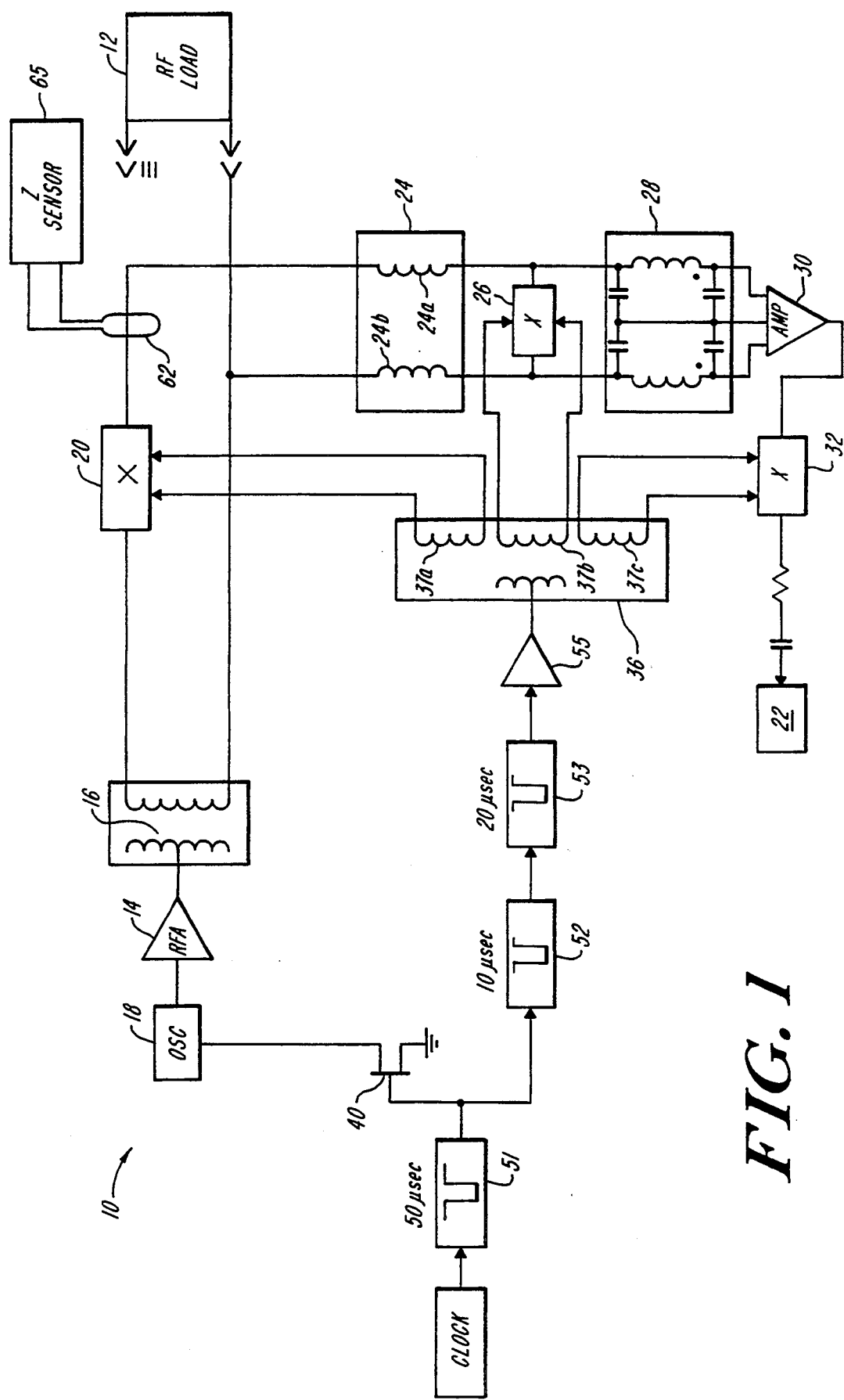
FIG. 1 is a functional illustration of an ablation catheter apparatus according to the invention.

As shown in FIG. 1, the cardiac ablation system 10 of the present invention has an ablation electrode 12, typically located at the distal tip of a special catheter (not shown) which is coupled to an RF amplifier 14 through a low impedance coupling 16. The low impedance coupling 16 is preferably a transformer having a ratio selected to achieve a specific level of the voltage delivered to the ablation electrode 12. The RF amplifier 14 is driven by an RF oscillator 18. A first switch 20 is connected between the low impedance coupling 16 and the ablation electrode 12. Switch 20 is opened by application of a signal developed on secondary winding 37a of a transformer 36, as discussed further below.

The ablation electrode 12 is also coupled, through a high impedance coupling 24, such as a pair of inductors 24a and 24b, to an electrode monitor 22. The high impedance coupling 24 electrically blocks RF energy originating at oscillator 18 from reaching the monitor or its pre-amp. A second switch 26 is provided across the two leads of the high RF impedance coupling 24, which connect via a low-pass filter 28 to an amplifier 30. A third switch 32 is connected between the amplifier 30 and the electrode monitor 22.

During operation of the RF power source, a current sensing loop 62 detects the instantaneous current, and a processing circuit 65 compares it to the ablation voltage and processes the signals to develop an instantaneous measure of tissue impedance across the catheter tip. Impedance sensing may be accomplished by conventional circuitry, and details thereof will not be further discussed herein.

Figures 2A, 2B:
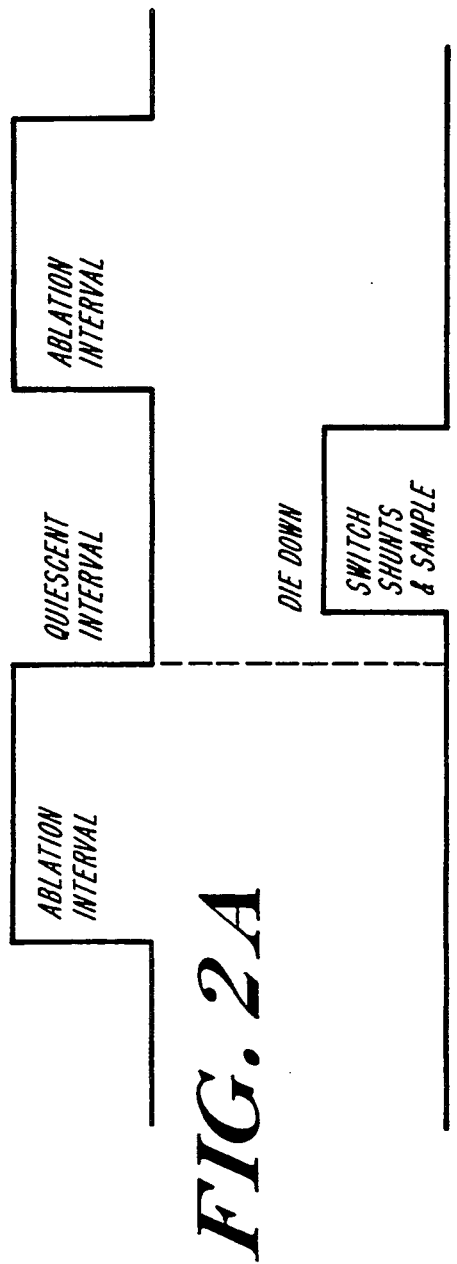
FIGS. 2A and 2B are timing diagrams representative of the switch timing of the invention.
Figure 3:
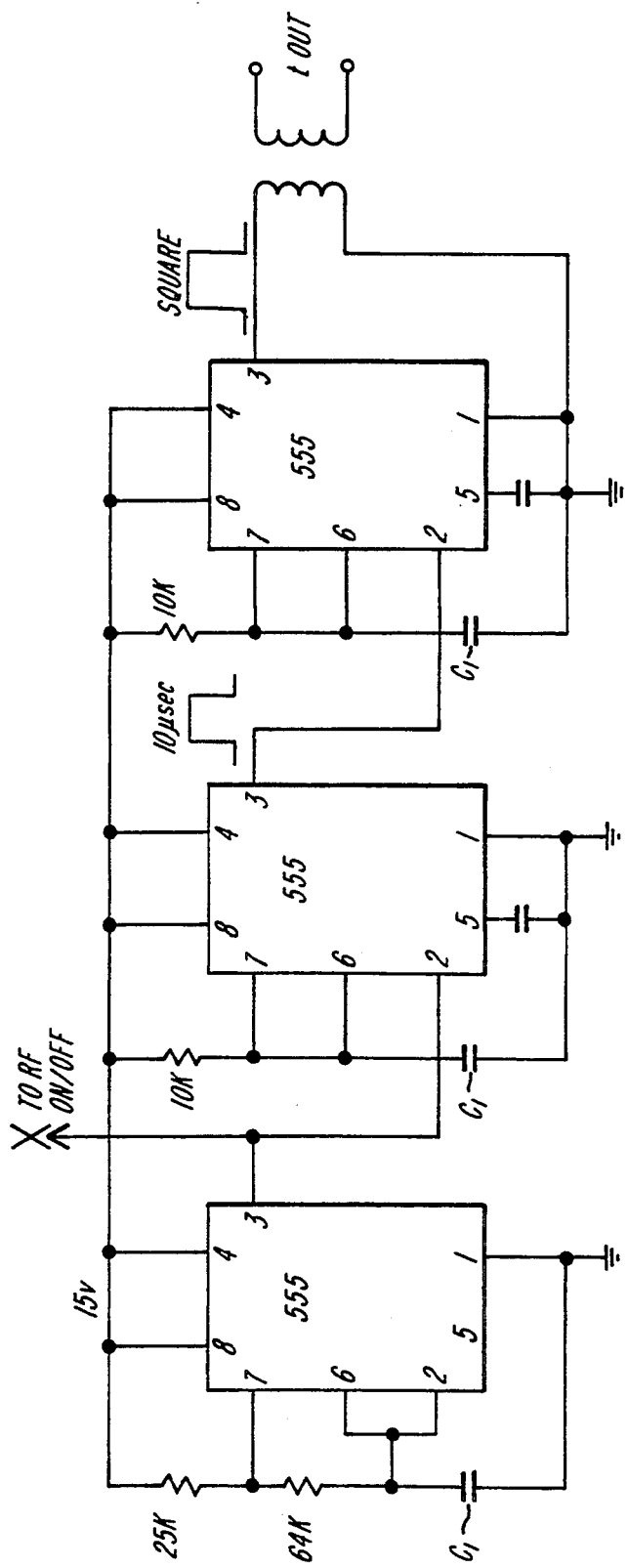
FIG. 3 is a schematic representation of the timing circuitry of FIG. 1.

FIG. 2 illustrates the timing of the three switches 20, 26 and 32. In broad outline, the timing circuitry 34 (as shown in FIG. 3) produces a set of on/off pulses which are coupled, e.g., by a transformer 36 to the three switches 20, 26, 32 during alternating and non-overlapping ablation intervals and quiescent intervals as shown in FIG. 2A. During ablation intervals, first switch 20 is closed to pass the RF power to the ablation electrode 12. The second switch 26, located beyond a pair of RF blocking inductors 24a and 24b, is also closed to shunt the high impedance coupling 24 and thereby isolate the coupling amplifier 30, and electrode monitor 22 from the high current appearing on the ablation electrode.

During the quiescent intervals the first switch 20 and the second switch 26 are opened, thereby removing the low-impedance winding of transformer 16 and the low impedance shunt 26 from the electrode circuit. Switches 20 and 26 are opened after an RF die-down interval during a period illustrated by the pulse in FIG. 2B. The third switch 32 is also switched, synchronized with the second switch 26, so that it is closed during an ECG sampling sub-interval of the quiescent interval. The third switch is closed, during a period illustrated by the pulse in FIG. 2B to pass the filtered endocardial signal to the electrode monitor 22, only after stray currents in the tissue and circuitry have died down.

As illustrated in FIG. 1, a system clock drives the first of three successive units 51, 52, 53 that determine the quiescent interval, die down interval, and sampling interval. Unit 53 provides a sampling interval defining pulse to a driver amplifier 55 that is transformer coupled to each switch. In general terms, a first timing pulse, defining a fixed ablation interval shown by way of example to have a fifty microsecond duration, is applied to the gate of a power field effect transistor 40 to provide power for one burst of RF ablation energy. During the ablation interval, switches 20 and 26 are closed. Thereafter, during the quiescent interval, transistor 40 turns off, and after a brief RF die-down interval, a twenty microsecond pulse is applied to the transformer coupling 36 to simultaneously open switches 20 and 26 and close switch 32. Alternatively, an additional pulse (FIG. 2C) may be supplied to close switch 32 during a later part of the twenty microsecond interval to pass an amplified sample of the endocardial signal to the monitor 22 after all stray currents in the tissue and circuitry have died down and amplifier 30 has stabilized.

This operation is advantageously obtained as illustrated in FIG. 3, using several 555 timing chips with suitable resistors and capacitors to successively define the basic timing interval described above.

Figure 4:
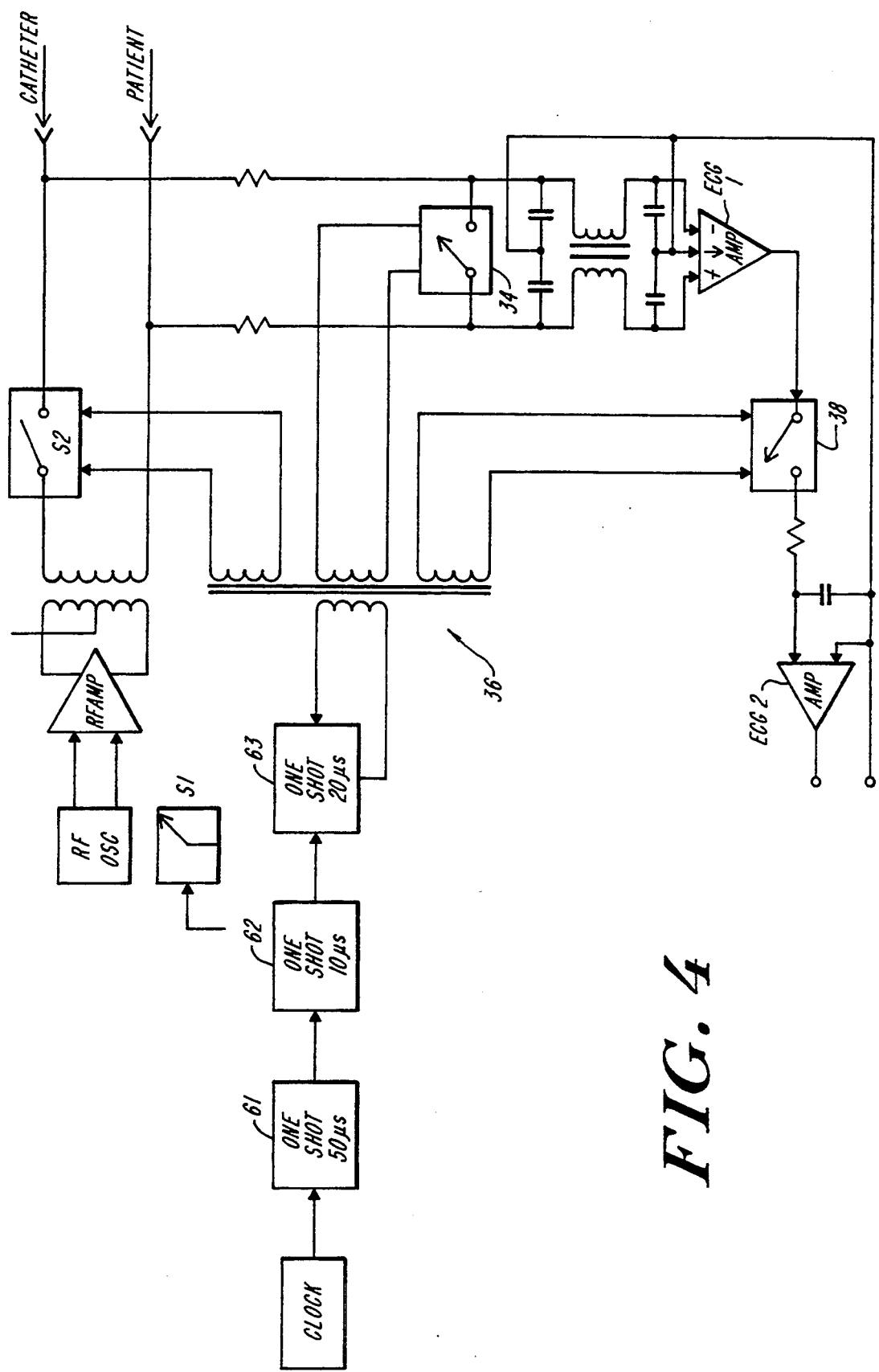
FIG. 4 is a schematic block diagram of another embodiment of the invention.

FIG. 4 is another schematic block diagram of the invention. In this diagram, components are identified with the same reference characters as used for comparable elements of FIG. 1. Power FET, and switches 20, 26 and 32 correspond to switches $S_1$, $S_2$, $S_4$ and $S_3$, respectively, and the timing interval circuits 51, 52 and 53 correspond to power one-shots, 61, 62, 63. In this embodiment switch $S_3$ is seen to gate the input to a second stage ECG amplifier, increasing the overall signal to noise ratio. As before, one-shot 61 defines a basic quiescent interval, one-shot 62 defines an RF die-down interval of approximately ten microseconds, and one-shot 63 provides the actual switching control for switches $S_2$, $S_3$ and $S_4$. Switch $S_1$ is controlled directly by one-shot 61. The current sensing and impedance calculating elements are omitted for clarity. It will be understood that switch $S_3$ may be separately controlled to define a disjoint ECG sampling interval, following opening of $S_2$ and $S_4$.

In the presently preferred embodiment, the timing circuitry defines an "RF power on" ablation interval one hundred fifty microseconds in duration, with a ten microsecond RF die-down and a twenty microsecond endocardial sampling interval defined in successive sub-intervals of the fifty microsecond quiescent interval between ablation intervals. The ablation and quiescent intervals are repeated five thousand times per second, so that amplifier 30, switch 32 (or S3) and monitor 22 form a synchronous amplifier acting on five thousand samples of the endocardial signal per second. Monitor 22 preferably includes a specialized digital signal processor, of a type known in the art, which incorporates endocardial signal pattern detection and display modules to monitor the cardiac signals of interest and provide a visual and audible display of the arrhythmia as the cardiac site is undergoing the ablation treatment. Thus the cardiac muscle stimulation signals at the site of ablation are detected and displayed continuously during the ablation procedure, allowing immediate assessment of the accuracy of electrode placement as well as the degree or sufficiency of treatment. In this manner a more refined surgical intervention, with less incidental damage to adjacent tissue is achieved.

The invention has been described above in connection with certain illustrated embodiments. However, various additions, subtractions and modifications can be made by those skilled in the art without departing from the spirit of the invention, and are within the scope of the claims.

The following claims are intended to cover all generic and specific features of the invention, including those objects set forth above and made apparent from the preceding description and accompanying drawings, as well as such modifications thereto within the scope of the invention, as will occur to those skilled in the art.

What is claimed is:

1. An improved system for cardiac ablation to inactivate a tissue site of cardiac arrhythmia, such system including an ablation catheter having an ablation electrode, a low impedance coupling for connecting the ablation electrode to an ablation power source, and an electrode monitor for receiving action potential signals developed across a sensing electrode and producing an output indicative thereof, and further comprising:

high impedance coupling means for interconnecting the sensing electrode to the electrode monitor, a plurality of switch means, including a first switch connected between said low impedance coupling and said ablation electrode, and a second switch connected between said electrode monitor and said high impedance coupling means, for selectively interconnecting said ablation power source and said electrode monitor to the ablation catheter, and timing means for synchronizing operation of said plurality of switch means to define ablation intervals and quiescent intervals, wherein said ablation electrode is also said sensing electrode, and said timing means synchronizes operation to disconnect said low impedance coupling from said ablation electrode and pass a sample of action potentials at the tissue site to said electrode monitor during each quiescent interval, both the ablation intervals and quiescent intervals alternating with each other at a frequency above 500 Hz such that ablation and monitoring occur continuously and appear to be performed simultaneously.

2. An improved system according to claim 1, further including a signal processing means connected between said second switch and said electrode monitor for processing action potentials passed to said electrode monitor.

3. An improved system according to claim 1, wherein said plurality of switch means further includes a third switch connected between said high impedance coupling means and said electrode monitor, for passing action potentials to said electrode monitor during an ECG sampling interval within the quiescent interval, said third switch being switched in synchronization with said second switch by said timing means.

4. An improved system according to claim 3, including a low-pass filter coupled between said second switch and said third switch.

5. An improved system according to claim 4, further including an amplifier coupled between said low-pass filter and said third switch.

6. An improved system according to claim 5, wherein said second and third switch are operated by said timing means to shunt an input and to pass an output of the amplifier in separate time intervals thereby enhancing quality of a signal provided to the electrode monitor.

7. An improved system according to claim 1 further including an ablation power source in circuit with said low impedance coupling, wherein said ablation power source includes means for providing a square wave RF signal to said ablation electrode.

8. An improved system according to claim 7, wherein said means for providing provides a square wave RF signal with an amplitude of about 50 Volts.

9. An improved system according to claim 7, wherein said means for providing provides a square wave RF signal with an amplitude of less than 100 Volts.

10. An improved system according to claim 1, wherein the ablation catheter includes a catheter tip, and said ablation electrode is mounted in the catheter tip to deflectably contact adjacent tissue.

11. A method for performing cardiac ablation to inactivate a tissue site of a cardiac arrhythmia signal, comprising:

a step of delivering ablation energy to the tissue site during plural repetitive ablation intervals, and a step of monitoring action potentials at the tissue site during plural repetitive quiescent intervals, wherein said steps of delivering and monitoring are both performed, using a catheter tip electrode, in non-overlapping intervals that alternate with each other at a repetition rate substantially above a Nyquist sampling rate for faithfully representing the cardiac arrhythmia signal continuously as ablation energy is being applied.

12. A method according to claim 11, wherein the step of delivering ablation energy is performed by transmitting ablation energy through a low impedance coupling to the catheter tip electrode, and the step of monitoring is performed by connecting said electrode through a high impedance coupling to a monitor, and further comprising a step of disconnecting the low impedance coupling during the quiescent intervals.

13. A method according to claim 12, further comprising the step of shunting across the high impedance coupling during ablation intervals.

14. A method according to claim 11, further wherein said quiescent intervals occur at least 1,000 times a second.

15. A method according to claim 11, further wherein said quiescent intervals occur about 5,000 times a second.

16. A method according to claim 11, further wherein said quiescent intervals occur less than 10,000 times a second.

17. A method according to claim 11, further wherein each of said ablation intervals lasts about 150 microseconds.

18. A method according to claim 17, further wherein each of said quiescent intervals lasts a shorter time than said ablation intervals.

19. A method according to claim 11, further comprising the step of measuring an impedance of the tissue site during each of said ablation intervals.

20. A method according to claim 11, further comprising the step of pacing the heart at about 120 beats per minute during ablation and monitoring.

21. A method according to claim 11, further comprising the steps of monitoring signals to develop a cardiac signal indicative of cardiac motion and synchronizing application of ablation energy with a portion of the cardiac signal so that the heart is immobile during the ablation intervals.

22. An improved system for ablation of a cardiac tissue arrhythmia site, such system being of the type including an ablation catheter bearing electrodes for sensing cardiac signals and for ablating cardiac tissue, and (i) an electrode monitor and (ii) an ablation power source which are placed in circuit with tile electrodes for said sensing and ablating, respectively, the system further comprising circuit control means for effecting sensing and ablating in closely-spaced separate intervals wherein said circuit control means includes means for temporarily shunting the electrodes to shorten a charge die-down time between an ablation interval and a following sensing interval so that the sensing and ablating occur substantially continuously.

* * * * *

UNITED STATES PATENT AND TRADEMARK OFFICE
CERTIFICATE OF CORRECTION

PATENT NO. : 5,357,956
DATED : October 25, 1994
INVENTOR(S) : Paul C. Nardella

It is certified that error appears in the above-indentified patent and that said Letters Patent is hereby corrected as shown below:

Column 8, line 55, please replace "tile" with --the--

Signed and Sealed this

Seventeenth Day of March, 1998

Attest:

BRUCE LEHMAN

Attesting Officer

Commissioner of Patents and Trademarks